United States Patent
Dudek

[11] Patent Number: 5,523,053
[45] Date of Patent: Jun. 4, 1996

[54] STERILIZATION METHOD AND APPARATUS FOR SPICES AND HERBS

[75] Inventor: Daniel H. Dudek, Cockeysville, Md.

[73] Assignee: Newly Weds Foods, Chicago, Ill.

[21] Appl. No.: 260,068

[22] Filed: Jun. 15, 1994

[51] Int. Cl.⁶ .................. A61L 2/06; A23L 3/18; F26B 17/12
[52] U.S. Cl. .................. 422/26; 422/295; 422/308; 99/483; 426/320; 426/521; 34/171
[58] Field of Search .................. 422/26, 32, 33, 422/295, 307, 308; 99/483; 426/521, 476, 320; 34/168, 170, 171, 402, 403; 435/304, 311

[56] References Cited

U.S. PATENT DOCUMENTS

| | | | |
|---|---|---|---|
| 4,064,646 | 12/1977 | Lödige et al. | 426/521 X |
| 4,147,098 | 4/1979 | Witte | 99/483 X |
| 4,210,678 | 7/1980 | Bayusik et al. | 426/521 |
| 4,539,903 | 9/1985 | Sugisawa et al. | 99/470 |
| 4,563,263 | 9/1985 | Goldhahn | 426/520 |
| 4,844,933 | 7/1989 | Hsieh et al. | 426/521 |
| 5,344,609 | 9/1994 | Long | 422/308 X |

*Primary Examiner*—James C. Housel
*Assistant Examiner*—E. Leigh Dawson
*Attorney, Agent, or Firm*—Joseph P. Katrick

[57] ABSTRACT

To avoid premature deterioration of raw products such as spices and herbs or products produced with these ingredients, the product or material is sterilized by exposure to elevated pressures and temperatures for a predetermined time. The sterilization process comprises a multiplicity of chambers whereby a product is introduced to the first chamber, pressurized, transferred through a series of sterilization chambers while exposing the product to the sterilization environment of the chambers for a predetermined time, then depressurized in a depressurization chamber. When using a moist sterilization fluid, a drying chamber is attached to the depressurization chamber to remove excess and undesirable moisture from the product.

19 Claims, 2 Drawing Sheets

STERILIZATION METHOD AND APPARATUS FOR SPICES AND HERBS

BACKGROUND OF THE INVENTION

1. Field of the Invention

The present invention relates to a process and apparatus for sterilizing materials and products including foodstuffs, more particularly to improvements in the method of sterilization of spices and dry herbs. In addition, this invention relates to an apparatus and method which achieves better control of the sterilization process, allows for much easier cleaning, and results in a more satisfactorily sterilized product.

2. Description of the Related Art

It has been known for many years that sterilization of grains was necessary in order to reduce microbial counts to a satisfactory level. In fact, for wheat grain, a microbial count of less than 5,000 per gram is necessary to prevent deterioration of refrigerated doughs for biscuits, dinner rolls, cookies, pizza, coffee cake and the like. This level differs quite markedly from typical counts of 100,000 or higher prior to treatment.

Paralleling the need for reducing the microbial counts in grains, the spices and herbs which are important ingredients in these convenience and fresh refrigerated foods must also be sterilized in order to avoid microbiological spoilage of these foods.

Methods which have been employed to reduce microbial populations include washing, heating, treating with fumigants, disinfectants, or chemical sterilants; irradiation with ultraviolet light; exposure to ozone; radio frequency or dielectric heating; treatment with sonic and supersonic vibrations; and irradiation with gamma rays, electron beams, or X-rays. Treatment with ethylene or propylene oxide has also been effective but has come under great scrutiny by governmental agencies, requiring reduction of residual chemical in the product by repeated cycles of aeration, heating, and evacuation. In fact, sterilization with ethylene oxide has been forbidden in some European countries because of it's toxic nature.

Heating as a means of controlling microbial population has advantages over other methods in that no chemicals are added to the product, no food regulations are involved, whole spices and herbs of high microbiological population can be treated effectively, and equipment for treating is conventional and readily available. The major drawback to using raw heat for sterilization is that substantial losses of volatile oils can occur or the product can easily be burnt, causing a flavor change, if exposed to the heat for too long or to an excessive temperature.

Traditionally, these treatment methods have been carried out in batches where part of the processing time was consumed in filling, removing, and cleaning. Additionally, unless all of the variables were very closely controlled between batches, the batches would differ from each other.

Further improvement in the method of treatment to reduce microbial (bacterial and fungal) counts centered around treatment by dipping in a hot solution of sanitizing agent, by indirect steaming, and by direct steaming.

Direct steam contact sterilization methods which have developed included continuous processes such as tubular screw conveyors where the product and the steam are introduced together and transferred the length of the screw conveyor. Shortcomings of this method include low capacity and the necessity for a steam-heated double jacket that is required to prevent the formation of condensation on the walls of the trough. Further, the inherent design of screw conveyors results in some unavoidable product damage because of the "pushing" effect on the product by the transfer mechanism.

Another direct steam sterilization method which developed involved use of a rotating drum with baffles creating a fluidized bed process. The throughput of this process improved over earlier designs but the residence time of the product with the steam could not be precisely controlled, allowing for undesirable results.

These high temperature short time (HTST) treatments with steam pressure has been shown to be an effective sterilization process for spices and herbs, producing a satisfactory product from a bacteriological, as well as other (color, flavor, etc.), point of view.

During this sterilization process the moisture content of the spice or herb increases due to the direct steam infusion and condensation of the steam vapor on the product. In order to avoid microbiological spoilage of the product due to this higher moisture content, the product typically has to be dried and cooled after the process.

U.S. Pat. No. 3,994,685 discloses a two-stage process where material to be sterilized is rapidly and uniformly heated to the desired temperature while being vigorously mixed with the sterilizing agent by means of a mechanical agitator. In the second stage of this process, the material is kept at the desired sterilization temperature for a predetermined length of time, remaining virtually stationary since no mechanical devices such as stirrers or mixers are employed in this stage. This Patent discloses that the second stage may include multiple layers of material that correspond to the individual batches introduced from the first stage. The Patent also discloses that the material is to be removed from the second stage by gravity means where each layer of material corresponding to a batch from the first stage is removed after the appropriate treatment time. In practice, because of uncontrollable variations in the gravity flow, the second stage treatment time can vary, thus it is possible that some portions of the product will remain unsterilized. In addition, since the material remains in an unagitated state and in contact with steam for some period of time in the second stage, caking, nesting, and material buildup on the container walls will be difficult to prevent.

U.S. Pat. No. 4,563,263 discloses a continuous sterilization and cooling apparatus and method. In this Patent, the pressurized steam treatment chamber is directly coupled to a pressurized cooler where hot material that has been discharged from the treatment chamber is cooled by direct contact with a coolant fluid. The object of this invention was to provide an apparatus and method for removing particulate matter from a pressurized steam treatment chamber while preventing flashing, disintegration, attrition, and mushing. It is apparent that the drawbacks of this disclosure include difficulty assuring that each particle of the product was treated for only the proper length of time at the right temperature. Additionally, this apparatus contains many moving mechanical parts which make effective and efficient cleaning very difficult.

U.S. Pat. No. 4,844,933 discloses a process and apparatus for sterilization of spices and leafy herbs where culinary steam is injected into a vessel while the contents are being mechanically agitated by an array of paddles. The process is a batch operation where the material is first introduced into the vessel, sterilizing steam is introduced into the vessel and the material is exposed to this steam for a predetermined time. When this time limit has been achieved, the material is transferred to a second adjoining vessel where it is cooled. Transfer of the material between the various vessels is achieved through pressure differentials. The methods employed to transfer and sterilize the product involve substantial physical manipulation which may tend to change the nature of the product. Additionally, product can collect in various corners of the equipment making cleaning relatively difficult.

In summary, various continuous process sterilization methods are already known. Some devices utilizing these methods contain baffles designed to insure that the product being treated remains in the apparatus for the minimum length of time needed for sterilization. Other designs depend on a fluidized bed to transfer the product through the treatment apparatus. However, in practice, the treatment time cannot be guaranteed since particles may pass through the apparatus quicker than intended resulting in inadequate sterilization. Also, the converse may occur where the particles remain in the apparatus longer than intended causing undesirable changes to the qualities of these particles. Additionally, many of the steam sterilization methods are utilizing wet steam which requires higher pressures and longer treatment time. For all steam treatment processes presently known, cleaning can only be accomplished by either opening access plates or disassembling the apparatus to remove residual particles for a changeover to a different material.

3. Objects of the Invention

Accordingly it is an object of the present invention to provide an improved continuous sterilization method and apparatus for spices, herbs and the like.

A further object of the invention is to provide a sterilization method and apparatus wherein the contact time of the material with the hot gas is effectively and very closely controlled thus optimizing the sterilization through processing every particle for the same period of time while concurrently minimizing undesirable side effects such as flavor change and allowing for exact repeatability between loads.

Another object is to agitate the material adequately as it is being sterilized so that sterilization can be accomplished efficiently, reliably, and thoroughly.

Another object is to provide an apparatus that minimizes the physical damage to the material as it is being processed.

Still another object is to utilize gravitational force to move the material through the apparatus.

Another object is to provide a process and apparatus where the environment and time required to process can be easily changed to suit the requirements of the material being processed.

Still yet another object is to design an apparatus that achieves positive and continuous cleaning as well as vastly shortened time for cleaning during a changeover.

Another object is to utilize the latent heat of steam for the sterilization process.

Yet another object is to design an apparatus which can be utilized to efficiently sterilize many different spices and herbs with easy changeover and minimal cleaning.

Additional objects, advantages and novel features of the invention will be set forth in part in the description which follows, and in part will become apparent to those skilled in the art upon examination of the, following or may be learned by practice of the invention. The objects and advantages of the invention may be realized and attained by means of the instrumentalities and combinations particularly pointed out in the appended claims.

SUMMARY OF THE INVENTION

According to the present invention, the foregoing and other objects and advantages are attained through a method of sterilization which utilizes a series of chambers to treat a material. In the best mode, it is envisioned that the series of chambers are mounted in a vertical fashion in order to utilize the benefits of gravity to transfer the product between chambers.

A product to be sterilized, such as a dry herb or spice, is introduced into the first chamber and the chamber is sealed. This chamber is then pressurized to match the fluid pressure of the sterilization agent that will be applied to the product during the subsequent sterilization. The dump valve or slide valve located at the bottom of this chamber is opened and the contents of this chamber gravity flow into the adjoining chamber.

This adjoining chamber is sealed and a sterilization agent, typically dry steam, is introduced into this chamber allowing the product to be exposed to this hot gas for a specific time period.

This treatment process is repeated a multiplicity of times in subsequent chambers until the product has been exposed to the hot gas for a predetermined period of time based on the characteristics of the particular product undergoing sterilization.

For spices and herbs, total treatment time for the sterilization process which will include the sum total time of exposure in all of the chambers, will typically be in the range of 10 seconds to 1 minute. Typical chamber pressures for spices and herbs will be in the range of 5 to 50 psig and sterilization temperature will fall in the range of 180 to 300 degrees Fahrenheit. Because of the flexible design of the apparatus, these times, temperatures, and pressures can be varied to suit the requirements of the material being sterilized.

Because of the minimal time required to sterilize certain products, exposure time of the material to the sterilization environment must be precisely controlled in order to prevent undesirable product changes. Through use of a multiplicity of chambers, the exposure time can be controlled very accurately. Depending on the residence time required to treat a specific product, adjoining chambers may be concurrently used in a manner very similar to opening moveable partitions in a conference room to allow for concurrent utilization of adjoining sections. This can easily be achieved by maintaining selected dump valves or slide valves in the open position thereby reducing the effective number of chambers.

The method and apparatus of the invention, using an accurately timed series of chambers, will sterilize any product or material for a very precise amount of time. The potential for under- or over-exposure of the product or material to the sterilization agent is almost impossible. In addition, problems such as caking and nesting are minimized as a result of the relatively continuous transfer of product or material through the series of chambers.

To greatly reduce the time for cleaning or changeover as compared to other designs, all of the dump or slide valves can be simultaneously opened by overriding the gate or dump value controls, thereby allowing for visual inspection or cleaning of the entire apparatus at one time. Thus, this design eliminates the need for opening access plates or partially disassembling the apparatus to accomplish effective cleaning or inspection.

Still other objects and advantages of the present invention will become readily apparent to those skilled in the art from the following detailed description, wherein I have shown and described only the preferred embodiment of the invention, simply by way of illustration of the best mode contemplated by me of carrying out my invention. As will be realized, the invention is capable of other and different embodiments, and its several details are capable of modifications in various obvious respects, all without departing from the invention. Accordingly, the drawing and description are to be regarded as illustrative in nature, and not as restrictive.

DESCRIPTION OF THE PREFERRED EMBODIMENTS

Figure 1:
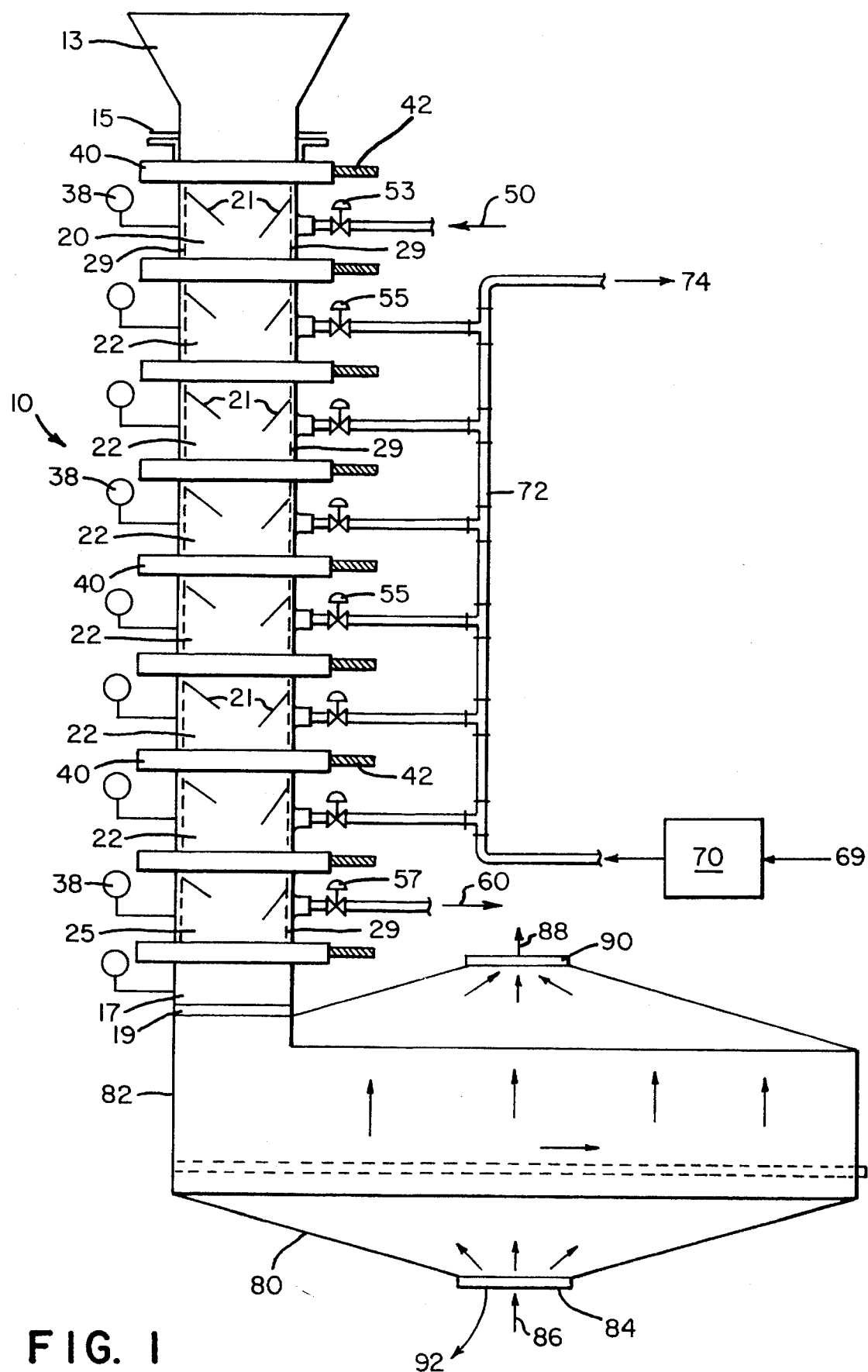
FIG. 1 is a schematic illustration of the apparatus used in carrying out the method of the present invention.

Referring now to the drawings more particularly to reference numbers wherein like numerals designate corresponding parts throughout the several views, in FIG. 1 there is shown a sterilizing apparatus which is designated generally by the number 10 comprising a series of chambers 22 constructed according to the teachings of the present invention.

In the preferred embodiment, the apparatus 10 also comprises a feed hopper 13 which is sealingly engageable with a flange 15 for inlet to a pressurization chamber 20. This pressurization chamber 20 is physically located as the uppermost chamber of the apparatus and is the first chamber for the introduction of product to be processed. This pressurization chamber 20 serves as a pressure lock for the product entering the apparatus through the feed hopper 13 and allows the product to be brought to the same pressure utilized for the sterilization prior to introduction of the product to the first and uppermost sterilization chamber 22. With the upper and lower dump or slide valves 40 of the pressurization chamber closed, a fluid 50 is introduced into the closed chamber 22 to accomplish the pressurization, the rate and timing of this fluid flow being controlled by a valve 53. This fluid 50 may be either the sterilization agent utilized in the sterilization chambers, pressurized air, or any other fluid which is compatible with the sterilization agent. Through use of this pressurization chamber, the sterilizing environment of the series of sterilization chambers 22 can be maintained at or near the desired sterilizing condition with reduced effort and reduced need to add additional pressurized steam.

Also in the preferred embodiment, the apparatus 10 further comprises a depressurization chamber 25 physically located beneath the multiplicity of sterilization chambers 20. This depressurization chamber 25 follows the last chamber of the sterilization process and is utilized to depressurize the product which has been sterilized to atmospheric pressure in a controlled manner, the depressurization being controlled by a valve 57 which exhausts the pressurized fluid 60. The rate of depressurization varies depending on the product being sterilized and it is intended that this depressurization rate be sufficiently slow to avoid puffing or other damage to the product. Similar to the pressurization chamber, the depressurization chamber reduces the need to add steam or pressure to the sterilization process and allows the process to be controlled more closely through maintaining better control of the sterilization parameters of time and temperature.

Between each of the chambers a dump or slide valve 40 is mounted in communication with adjoining chambers. When the valve 40 is in the closed position, this valve will serve as a seal between chambers, isolating the chamber and its contents from adjoining chambers and the contents of these chambers. When both upper and lower valves 40 of a chamber are in the closed position, a sealed chamber 20, 22, or 25 is formed. These valves 40, which can be program operated, are moved by actuating devices 42 which physically control the opening and closing of the valves 40, allowing the valves to open and close at the proper time pursuant to the requirements of the product being processed. To effectuate quick inspection or cleaning of the entire apparatus, all of the valves can be programmed to remain open simultaneously in order to accomplish the inspection or cleaning.

To accomplish complete and equal exposure of all particles to the sterilizing agent, fixed or moveable baffles 21 may be selectively installed in the chambers 20, 22, and 25 to assist in agitating the product either during residence in a chamber or as the product transfers to a subsequent chamber.

A sterilizing agent 69, preferably pure process steam, known to those skilled in the art as steam which contains no contaminants, is introduced into a distribution system 72 for introduction into the sterilizing chambers 22 through control valves 55. This sterilizing agent 69 is metered through these valves into the sterilization chambers 22 when pressure sensing devices 38 determine that additional fluid 69 is needed to maintain the desired pressure. The valving, any flow control devices, and temperature or pressure sensing devices are well known to those skilled in this art and are generally omitted from the drawings for the sake of clarity. To improve the efficiency of the steam sterilization, decrease and control moisture transference to the product, and minimize the risk of burning or charring the product, a steam drier (separator) 70 is installed in the steam supply line to remove excess moisture from the steam supply 69. To further improve the efficiency as well as improve the ability to maintain the sterilization chamber 22 temperature, the chambers 22 can be constructed with spaced wall portions to form a jacket 29. Steam can then be circulated through this jacket 29 thereby allowing the chamber temperature to remain more consistent.

The steam pressure in the jacket 29 should not be of higher pressure than the steam 69 utilized in the chambers 22. If the jacket 29 pressure is allowed to become higher than the chamber 22 pressure, superheating of the steam in the chambers will occur. If superheating were to occur, the material being sterilized may be damaged and sterilization will be prevented since the chambers 22 become, in effect, a hot air oven, which requires a much higher temperature and considerably longer period of exposure to effect sterilization.

When steam 69 is utilized as the sterilizing agent in the sterilization chambers 22, some moisture from the steam will condense on the material or product being treated during the sterilization process creating a moist product or material. To prevent caking, deterioration, or spoilage of the product or material as a result of the additional moisture, a drying chamber 80 is installed to remove this excess moisture from the sterilized material. In the preferred embodiment, this drying chamber 80 will be physically located near the depressurization chamber and sealingly engageable 19 with the discharge 17 of the depressurization chamber.

A dry sterile fluid 86 is introduced into the drying chamber 80 through opening 84 and allowed to communicate with the sterilized but moist material. This fluid may be heated to assist in drying the material but heating of this fluid 86 will be dependent on the amount of moisture which must be removed. The dry sterile fluid 86 will typically flow countercurrent to the flow of material and increase in moisture content as the contact time with the material increases. The moisture laden sterile fluid 88 will normally discharge the drying chamber through the upper opening 90 and, depending on the fluid used, may be dried and reused again for further drying. After the product or material has been adequately dried in the drying chamber 82, it is discharged 92.

Figure 2:
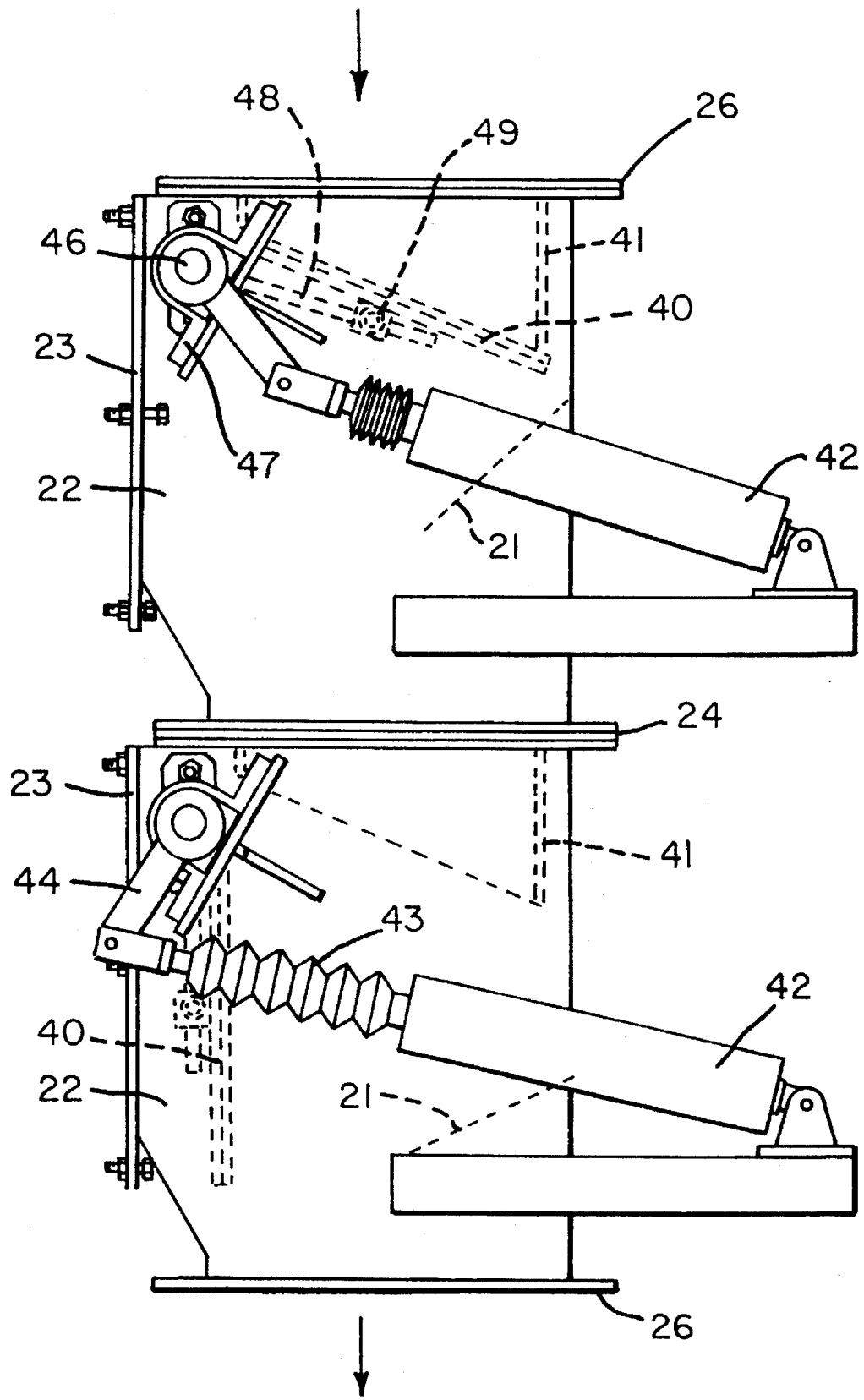
FIG. 2 is a more detailed view of two typical adjoining sterilization chambers of the sterilization system of the present invention.

FIG. 2 shows a more detailed view of two adjoining sterilization chambers 22 and mounting flanges 26 which are utilized to sealingly engage adjoining chambers 24. FIG. 2 also shows a particular dump valve assembly integral to these chambers 22 and utilized in one of the preferred embodiments. In the closed position as depicted in the upper chamber of FIG. 2, the dump valve 40 is seated against the valve seat 41. The dump valve is controlled by an actuator 42 which may a pneumatic or hydraulic cylinder. This rod is pivotably connected to a crank arm 44. The crank arm 44 is rigidly fastened to a rotatable shaft 46. This shaft is mounted to the sterilization chamber by means of bearings 47. A control arm 48 is rigidly attached to the rotatable shaft 46 at its end. The opposite end of the control arm 48 is slideably connected to the dump valve by means of a slide block 49.

When fluid pressure is applied to the actuator 40, the cylinder rod 43 extends from the cylinder 42. As this rod 43 extends, it causes crank arm 44 to rotate, the rotation of this arm 44, in turn, causes the shaft 46 to rotate. As the shaft 46 rotates the control arm 48 also rotates. Because of the slidable connection to the dump valve 40 through the slide block 49, the dump valve is caused to move as the result of rotation of the control arm 48. When the actuating device 42 is actuated the dump valve moves from the closed position shown in the upper chamber of FIG. 2 to the open position as shown in the lower chamber of FIG. 2. When the actuating signal is removed or when pressure is applied to the opposite end of the actuating device 42, the dump valve returns to the closed position.

In other preferred embodiments, slide valves may be utilized instead of dump valves 40 as described above. These slide valves typically comprise a plate which, when actuated, slides along guides to either the open or closed position instead of pivoting from an open or closed position to the other position.

It will be appreciated by those skilled in the art that the precise temperature of the steam and length of retention in the sterilizing chambers 22 will depend on the characteristics of the material being sterilized. Reaction of the product in terms of retention of volatile oils as well as appearance will depend on the material undergoing sterilization and will vary from one material to another.

From this required variation of treatment time for different materials, it will be apparent to those skilled in the art that the entire sterilization process from the time of loading the material into the pressurization chamber to the discharge from the depressurization chamber can be very efficiently and precisely controlled by means of a computer to obtain the highest quality, most effectively sterilized material while maximizing material throughput. Additionally, use of a computer will allow real time adjustment of the process time not only when changing to another material for sterilization but also during the processing of a single material allowing minor adjustments as necessary to finely control the quality of the material being processed.

Because the exposure time to high pressures and sterilizing temperatures can be very precisely controlled with this invention, the volatile oils in herbs and spices that would otherwise be lost will now remain in the material enhancing both the flavor and appearance of the material after the sterilization process.

The steps of the process of the present invention utilizing the foregoing apparatus will now be described.

According to a preferred method, steam 69 is introduced into the sterilizing chambers 22 preconditioning these chambers prior to the introduction of a material to be sterilized. Prior to the start of a sterilizing cycle, a charge of product or material is introduced into the apparatus through feed hopper 13. Dump valve 40 located at the top of the pressurization chamber 20 opens while the dump valve 40 at the bottom of the pressurization chamber remains closed. The charge of material falls by gravity into the pressurization chamber 20. The dump valve 40 at the top of the chamber closes and a pressurization fluid 50 is introduced into this chamber allowing the chamber and its contents to match the sterilization pressure of the subsequent sterilization chambers 22. After pressure is approximately equalized, the dump valve 40 located at the bottom of the pressurization chamber opens allowing the charge of material to enter the first sterilization chamber. The dump valve 40 at the top of the first sterilization chamber closes while the valve 40 at the bottom of this chamber remains closed. Any deficiency in steam pressure in this chamber is remedied through release of steam 69 through control valve 55.

The process of the first sterilization chamber is repeated a multiplicity of times through subsequent chambers in the sterilization column until the material has been effectively sterilized for the requisite time. Upon release of the product into the pressurization chamber 20 and the closing of the dump valve 40 at the top of this chamber, it is envisioned that another charge of material is loaded into the hopper 13 so that this charge may closely follow the preceding charge when the pressurization chamber empties into the first sterilization chamber. By keeping the chambers full and material continuously moving between chambers, the process can very closely approximate a continuous process.

Upon completion of the exposure to the sterilization treatment of the multiplicity of chambers, the material is discharged into a depressurization chamber 25. Upon closing the dump valve at the top of this chamber while the lower valve remains closed, the depressurization valve 57 is opened, the pressurized fluid 60 is released, and the pressure in this chamber 25 is controllably reduced to atmospheric pressure. Upon reaching atmospheric pressure, the lower dump valve 40 of this chamber is opened and the material is discharged into the drying chamber 82. The lower dump valve 40 of the depressurization chamber 25 is then closed in anticipation of another charge of material while the material which has been discharged is dried by exposure to dry sterile fluid 86 in the drying chamber 82. Upon adequate drying, the dry sterile material is discharged 92 from the apparatus.

I claim:

1. A method for sterilizing whole spices and herbs comprising the steps of:
   (a) introducing a material to be sterilized into a first and uppermost chamber;
   (b) sealing and pressurizing said first and uppermost chamber containing the material;

(c) discharging the material by gravity into a next lower adjoining pressurized chamber;

(d) sealing said adjoining pressurized chamber and introducing pressurized sterilizing fluid into said adjoining chamber;

(e) repeating steps (c) and (d) a multiplicity of times;

(f) discharging the sterilized material into a final chamber;

(g) depressurizing said final chamber;

(h) discharging the material from said final chamber.

2. The method as recited in claim 1, wherein the said depressurization and said discharge of the material from the final chamber occur simultaneously.

3. The method as recited in claim 1 wherein the material is agitated during introduction of the said pressurized sterilizing fluid.

4. The method as recited in claim 1, wherein the said pressurized sterilizing fluid in claim 1 (d) is steam.

5. The method as recited in claim 4, wherein the fluid used to pressurize the said first and uppermost chamber is steam.

6. The method as recited in claim 4, further comprising the step of drying the material after discharge from the final chamber.

7. The method as recited in claim 1, wherein the rate of depressurization in the said final chamber is controlled.

8. The method as recited in claim 1, further comprising agitating the contents of a chamber during discharge to a next lower adjoining pressurized chamber.

9. An apparatus for sterilizing whole spices and herbs comprising:

(a) a hollow column with an exterior surface and an interior surface, said interior surface surrounding and defining an interior space;

(b) means for dividing said interior space of said hollow column into a multiplicity of sealed chambers in vertical relationship to each other, said means being moveable to allow access between adjacent said chambers so formed;

(c) means for introducing a pressurized fluid into each said chamber so formed by said dividing means;

(d) means for controlling and opening the dividing means whereby a whole spice or herb in a said chamber drops by gravity into a next lower said chamber;

(e) a depressurizing chamber located at the bottom of said column.

10. The apparatus as recited in claim 9, further comprising means to control the rate of depressurization of said depressurizing chamber.

11. The apparatus as recited in claim 9, further comprising means for agitating the contents of a said adjacent chamber.

12. The apparatus as recited in claim 9, further comprising means for removing moisture from said pressurized fluid prior to said fluid being introduced into said chambers.

13. The apparatus as recited in claim 9, further comprising means for monitoring and controlling said pressurized fluid in the said chambers.

14. The apparatus as recited in claim 9, further comprising sensors for monitoring and means to maintain consistent temperature in the said chambers.

15. The apparatus as recited in claim 9, further comprising means for cleaning or inspecting said chambers whereby all said dividing means can be simultaneously opened to allow simultaneous access to the said interior space of said column.

16. The apparatus as recited in claim 9, further comprising a second hollow column surrounding said first column and having an interior and exterior surface, whereby said exterior surface of said first column and said interior surface of said second column form a space therebetween, a fluid source and a means for interjecting said fluid into said space.

17. The apparatus as recited in claim 16, wherein said fluid is steam.

18. The apparatus as recited in claim 9, further comprising a drying chamber attached to the discharge side of the said depressurization chamber whereby said drying chamber will remove excessive said pressurization fluid from the material passing through the apparatus.

19. The apparatus as recited in claim 9, further comprising an electronic programmable controller whereby said controller precisely controls the residence time of the material in each chamber through accurate control of the opening and closing of the said dividing means.

* * * * *

UNITED STATES PATENT AND TRADEMARK OFFICE
CERTIFICATE OF CORRECTION

PATENT NO.   : 5,523,053
DATED        : June 4, 1996
INVENTOR(S)  : Daniel H. Dudek It is certified that error appears in the above-indentified patent and that said Letters Patent is hereby corrected as shown below:

In claim 14, line 2, delete "means" and substitute --fluid valves--.

Signed and Sealed this

Twenty-third Day of September, 1997

*Attest:*

BRUCE LEHMAN

*Attesting Officer*    *Commissioner of Patents and Trademarks*